United States Patent
Konstantino et al.

(10) Patent No.: US 8,608,789 B2
(45) Date of Patent: Dec. 17, 2013

(54) DELIVERY SYSTEM FOR BIFURCATION STENTS

(75) Inventors: Eitan Konstantino, Orinda, CA (US); Tanhum Feld, Moshav Merhavya (IL)

(73) Assignee: Trireme Medical, Inc., Pleasanton, CA (US)

( * ) Notice: Subject to any disclaimer, the term of this patent is extended or adjusted under 35 U.S.C. 154(b) by 1707 days.

(21) Appl. No.: 11/439,707

(22) Filed: May 23, 2006

(65) Prior Publication Data

US 2007/0016279 A1 Jan. 18, 2007

Related U.S. Application Data

(60) Provisional application No. 60/684,624, filed on May 24, 2005.

(51) Int. Cl.
*A61F 2/06* (2013.01)

(52) U.S. Cl.
USPC ............................................................ 623/1.11

(58) Field of Classification Search
USPC ........... 623/1.11, 1.15, 1.16, 1.35, 1.23, 1.42; 604/284
See application file for complete search history.

(56) References Cited

U.S. PATENT DOCUMENTS

| | | | |
|---|---|---|---|
| 4,774,949 A * | 10/1988 | Fogarty | 606/108 |
| 4,994,071 A | 2/1991 | MacGregor | |
| 5,609,627 A | 3/1997 | Goicoechea et al. | |
| 5,724,977 A * | 3/1998 | Yock et al. | 600/437 |
| 5,749,825 A | 5/1998 | Fischell et al. | |
| 5,755,735 A | 5/1998 | Richter et al. | |
| 5,891,133 A | 4/1999 | Murphy-Chutorian | |
| 5,928,248 A | 7/1999 | Acker | |
| 6,048,361 A | 4/2000 | Von Oepen | |
| 6,099,497 A | 8/2000 | Adams et al. | |
| 6,165,195 A | 12/2000 | Wilson et al. | |
| 6,210,429 B1 | 4/2001 | Vardi et al. | |
| 6,221,098 B1 | 4/2001 | Wilson et al. | |
| 6,261,273 B1 * | 7/2001 | Ruiz | 604/284 |
| 6,325,826 B1 | 12/2001 | Vardi et al. | |
| 6,361,555 B1 * | 3/2002 | Wilson | 623/1.11 |
| 6,436,104 B2 * | 8/2002 | Hojeibane | 606/108 |
| 6,596,020 B2 | 7/2003 | Vardi et al. | |
| 6,599,316 B2 | 7/2003 | Vardi et al. | |
| 6,676,691 B1 | 1/2004 | Hosny | |
| 6,682,536 B2 | 1/2004 | Vardi et al. | |
| 6,689,156 B1 * | 2/2004 | Davidson et al. | 623/1.11 |
| 6,692,483 B2 * | 2/2004 | Vardi et al. | 604/529 |
| 6,706,062 B2 | 3/2004 | Vardi et al. | |
| 6,709,440 B2 | 3/2004 | Callol et al. | |
| 6,835,203 B1 | 12/2004 | Vardi et al. | |
| 6,884,258 B2 * | 4/2005 | Vardi et al. | 623/1.11 |

(Continued)

FOREIGN PATENT DOCUMENTS

| | | |
|---|---|---|
| DE | 29 708 803 U1 | 7/1997 |
| DE | 29 701 758 U1 | 3/1999 |
| EP | 1255506 B1 | 11/2002 |

*Primary Examiner* — S. Thomas Hughes
*Assistant Examiner* — Julie A Szpira
(74) *Attorney, Agent, or Firm* — Wilson, Sonsini, Goodrich & Rosati

(57) ABSTRACT

Systems for aligning and deploying side branch stents comprise a catheter having a side branch sensor at or near a distal end thereof. Methods comprises rotating and axially transitioning the catheter until the sensor is brought into alignment with an opening to the side branch vessel.

10 Claims, 4 Drawing Sheets

(56) References Cited

U.S. PATENT DOCUMENTS

| | | |
|---|---|---|
| 7,563,270 B2 * | 7/2009 | Gumm .................... 606/194 |
| 7,771,462 B1 | 8/2010 | Davidson et al. |
| 2002/0042650 A1 | 4/2002 | Vardi et al. |
| 2002/0156516 A1 | 10/2002 | Vardi et al. |
| 2002/0173835 A1 | 11/2002 | Bourang et al. |
| 2003/0004560 A1 * | 1/2003 | Chobotov et al. ........... 623/1.11 |
| 2003/0187494 A1 | 10/2003 | Loaldi |
| 2003/0195606 A1 | 10/2003 | Davidson et al. |
| 2004/0015227 A1 | 1/2004 | Vardi et al. |
| 2004/0019302 A1 | 1/2004 | Williams et al. |
| 2004/0133268 A1 | 7/2004 | Davidson et al. |
| 2004/0138737 A1 | 7/2004 | Davidson et al. |
| 2004/0267352 A1 * | 12/2004 | Davidson et al. ............ 623/1.15 |
| 2005/0010278 A1 | 1/2005 | Vardi et al. |
| 2005/0015108 A1 | 1/2005 | Williams et al. |
| 2005/0060027 A1 | 3/2005 | Khenansho et al. |
| 2005/0102019 A1 | 5/2005 | Yadin |
| 2005/0245941 A1 * | 11/2005 | Vardi et al. ................... 606/108 |
| 2006/0036218 A1 * | 2/2006 | Goodson et al. ............. 604/264 |
| 2006/0036315 A1 | 2/2006 | Yadin et al. |
| 2006/0047335 A1 * | 3/2006 | Israel ........................... 623/1.11 |
| 2006/0106448 A1 * | 5/2006 | Shaked ........................ 623/1.11 |
| 2006/0259116 A1 * | 11/2006 | Feld et al. .................... 623/1.11 |
| 2007/0219611 A1 * | 9/2007 | Krever et al. ................ 623/1.11 |
| 2008/0183269 A2 * | 7/2008 | Kaplan et al. ................ 623/1.11 |

\* cited by examiner

DELIVERY SYSTEM FOR BIFURCATION STENTS

CROSS-REFERENCES TO RELATED APPLICATIONS

The present application is a non-provisional of Provisional Application No. 60/684,624, filed May 24, 2005, the full disclosure of which is incorporated herein by reference.

The disclosure of this application is also related to that of U.S. patent application Ser. No. 11/330,382, filed on Jan. 10, 2006, the full disclosure of which is incorporated herein by reference.

BACKGROUND OF THE INVENTION

Field of the Invention

The present invention relates to medical methods and devices, more specifically to medical devices intended to treat stenoses in the vascular system at or near bifurcated lesions.

Stenting is a common medical procedure mainly directed at revascularzation of stenotic vessels where a blocked artery is dilated and a stent is placed to maintain vessel patency following the dilation. The stent is a small tubular device, usually a metallic mesh or other scaffold, that can be coated with drug or drug containing polymer.

While stents are successful in treating a variety of lesions in the vascular system, their success has been limited in the treatment of bifurcation lesions in the coronary and carotid arteries. Often the stent mesh at bifurcation lesion is jailing the side branch access and limiting blood flow to the side branch while interfering with the flow regimen.

Clinical literature describes the difficulties of using stents in treating bifurcated lesions. In addition to acute problems such as long procedural time, complications can also result from limited side branch access during procedure and the need to use conventional stents outside their design and labeling. The long term results are inferior and the rate of restenosis is high compared to other lesions.

Attempts have been made to design a dedicated stents and delivery methods for placing stents and bifurcated lesions in coronary and carotid arteries. However, current solutions suffer from a variety of shortcomings such as high profile relatively to conventional stents, the need for a cumbersome delivery system to place the stent at the right location and insufficiently accurate rotational positioning facing the side branch. Usually the side branch of the vessel is smaller than the main branch and the take off angle of the bifurcation varies. There is also a need for ostial side branch support and local drug delivery to the bifurcation area via stent coating.

Some of the prior art utilizes two guidewires to deliver and position the stent so that a side hole in the stent or a side portion area of the stent will face the side branch vessel. Examples can be seen in U.S. Pat. No. 5,749,825 Fischell et al., U.S. Pat. No. 5,755,735 Richter et al., U.S. Pat. No. 6,099,497 Adams et al., U.S. Pat. No. 6,596,020 Vardi et al., U.S. Pat. No. 6,706,062 Vardi et al., and U.S. Pat. No. 6,048,361 Von Oepen.

The need for two guidewires and frequently for two lumens to accommodate the guidewires requires a high profile system (i.e., a relatively large diameter) when compared to conventional stents and delivery systems and leads to difficulty in delivering the stent and longer clinical procedure. In many cases two guidewire bifurcation stent delivery systems require also larger guiding catheters than conventional stents delivery systems. In addition, the physician has a very limited ability to rotate the catheter to achieve rotational positioning, and the system must be guided to the location and radial position solely by the pre-placed guidewires. Due to the natural flexibility of the guidewires and the large difference between the guidewire diameter (usually 0.35 mm) and the side branch diameter (usually 2 mm or more), the positioning of the stent may not be accurate. The side portion of the stent may not be facing the central part of the side branch, and in many cases only a portion of the side hole or the side portion of the stent will face the side branch of the vessel. Attempts to improve alignment by using stiffer guidewires may result in other problems. For example, the conventional metallic guidewires affect the local geometry in the bifurcation site and mask the real bifurcation angle. Once the guidewires are pulled out at the end of the procedure, the side branch angle restores its original position sometimes leaving a gap between the stent and the arterial wall leading to inferior clinical outcome.

Other systems designed to deploy stents that provide at least partial support to the side branch opening utilize two balloons. Examples may be found in U.S. Pat. No. 4,994,071 (assigned to Cordis) in applications US 2005/0102019 and US 2005/0060027 assigned to Advanced Stent Technologies. Those systems suffer from complexity and the need to inflate two separate balloons, a high profile, and poor deliverability resulting from an excessive stack of material below the stent that add to the stiffness of the working end of the system.

When treating a bifurcation lesion using the above systems, the physician places one guidewire in the main vessel and a second guidewire in the side branch. This is done to maintain access to both vessels. A common problem associated with such use of two guidewires is that the guidewires tend to wrap around each other. This phenomenon is known as "wire crossing" and is very common when catheters needing two wires catheters are being used. Current bifurcated stent delivery catheters which utilize two guidewires and can not be delivered through such crossed wires. In some cases, the physician needs to retrieve the whole system including the guidewires, thus increasing the chances of morbidity and procedural complications. The physician has to rewire the arteries and start over with a new system.

For these reasons, the currently available delivery systems for bifurcation lesions are limited in performance and in the ability to accurately position the stent axially and ensure that the side portion or side hole of the stent are facing the side branch of the vessel. It would be desirable to provide catheter systems for delivering stents for bifurcation which need only a single guidewire for placement.

BRIEF SUMMARY OF THE INVENTION

This invention discloses a delivery system for bifurcated stents having side branch portion. The system comprises having a catheter single guidewire lumen with an expandable or other stent deployment shell or other stent deployment region near the distal end of the catheter used to deliver and deploy the stent with at least partial deployment of the side branch portion.

In one embodiment the catheter shaft is designed to rotate in response to torque applied by the operator.

In one embodiment the system includes a sensing mechanism to identify a side branch opening. Exemplary sensing mechanisms include an imaging component and a penetrating element which deploys laterally into the side branch when the stent is properly oriented toward the side branch.

In one embodiment the system is aligned by signals from the operator usually via electronic circuits. The distal part of the catheter is designed to rotate in response to the electronic signals. Markers can also be used to help accurately position the stent.

DETAILED DESCRIPTION OF THE INVENTION

The present invention provides a delivery system for bifurcated stents or other prostheses having a main body and a side branch portion or a side hole. The phrase "side branch portion" includes any opening or structure in the main body which is to be aligned with an ostium of a side branch lumen or vessel when the main body is in the main lumen or vessel. The side branch portion may be a simple hole in the form of a cell or a slit in the prosthesis structure which is preselected to be aligned with a side branch vessel but which is otherwise similar to other cells, slits, or the like in the prosthesis. More usually, however, the side branch portion will be an enlarged or enlargeable cell which is distinguishable from the adjacent or remaining structure of the prosthesis. In other embodiments, the "side branch structure" comprises a self-opening or balloon openable peripheral structure which is intended to bridge the circumference of the side branch ostium after the prosthesis is opened in the main branch. The bifurcated stents of this patent are suitable for placement at all types of bifurcated lesions and lesions near bifurcations in the vessels or ostial lesions of all types including aorto-ostial and anastomotic sites in which the side portion is located in one end of the prosthesis and will usually include flared portion.

The stents or other prostheses to be delivered in accordance with the present invention usually have a generally tubular structure comprising a main body that is capable of expansion by balloon inflation to support the main vessel and a side portion structure designed to expand at least partially into the side branch vessel and support the side branch ostium. Additional balloon(s) may be used to complete the deployment of the side branch portion or the main body of the stent if needed. Examples of suitable side branch stents and prostheses are provided in copending application Ser. No. 11/330,382 (022246-000240US), the disclosure of which has previously been incorporated herein by reference.

Figure 1:
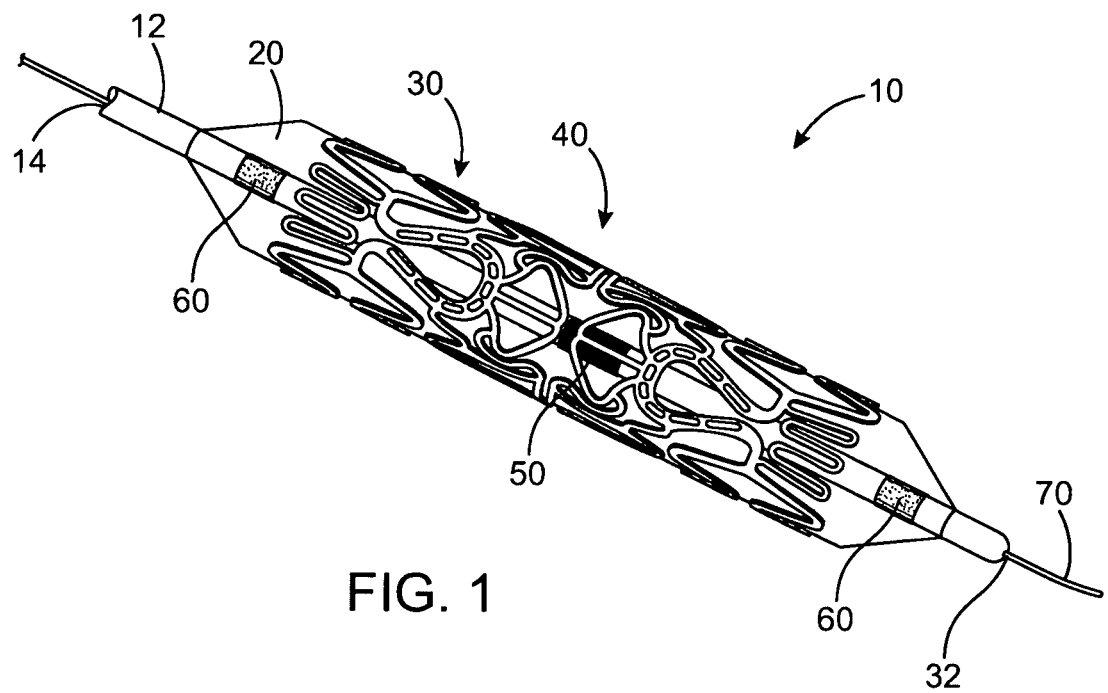
FIG. 1 is a general depiction of the catheter of the present invention with an undeployed bifurcation stent carried on a deployment balloon.
Figure 2:
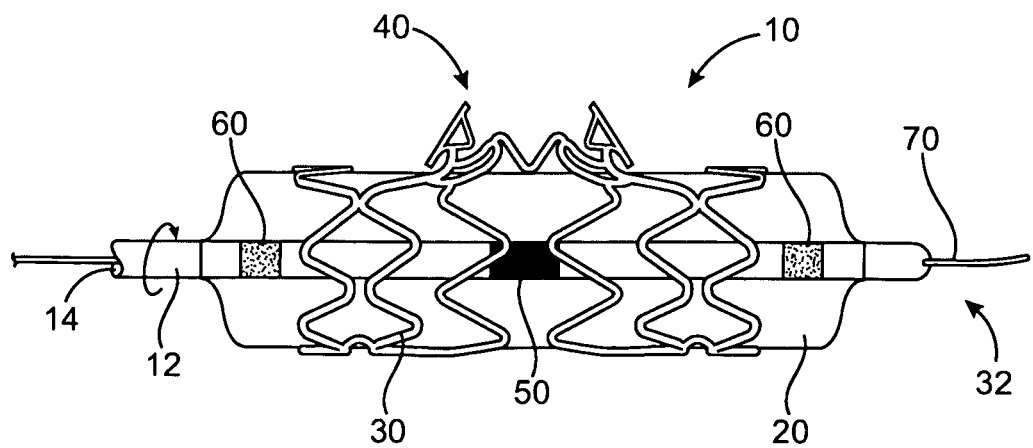
FIG. 2 is a general depiction of the stent of FIG. 1 after deployment.

An example of such a stent placed on a delivery catheter is shown in FIGS. 1 and 2. FIG. 1 shows a balloon catheter 10 having at least one lumen for receiving a guidewire 70 and a separate balloon inflation. A bifurcated stent 30 is crimped over balloon 20 with an unopened side branch portion 40 (FIG. 1). The side portion 40 will usually be formed integrally with the stent main body, but in other cases may be added to the stent main body using laser welding or any other attachment process. Catheter shaft 12 has sufficient torsional stiffness to rotate (arrow 14, FIG. 2) in response to torque applied at its proximal end 16 (FIG. 4) by the operator. This torque response can be achieved for example by using a braided shaft, stiffened shaft, hypotube or by using a suitable core wire or by other conventional methods used in the industry to improve the torque response of at least part of the shaft. The balloon 20 will usually be a conventional balloon (nylon blend, pebax blend, or the like) of a type used for the deployment of the stents and vascular prostheses. The side branch portion 40 is initially closed. To improve torque response and avoid uncontrolled motions ("whipping") of the distal end which could result from torque build-up in the shaft, damper sections (not illustrated) may be added to the shaft structure in a form of a non-braided section with mechanical properties different than the braided section.

FIG. 2 shows the stent 30 after expansion by the balloon 20 with the side branch portion open 40. The catheter shaft 12 has a single guidewire lumen 14 terminating at distal port 32. Conventional balloon markers 60 may be used to help the operator identify the location of the system in the vessel, and a sensing mechanism 50 such as an ultrasonic transducer, a laser diode, a semiconductor diode or other sensor, can be used to help orient the system and determine the location of the side branch.

In one embodiment the sensing mechanism 50 comprises an imaging component including at least one fiber optic (or other common laser light transmission element) located at or near the side branch portion 40, typically on the circumference of the distal end of the catheter shaft 12, preferably near or on the balloon 20 in the case of self expandable stents or other prostheses. Light or other detectable radiation can be transmitted through the fiber optic system and reflections can be detected by the fiber optic system to help locate the branch. Laser radiation reflected back from different parts of the vessel wall can be monitored to identify changes in the vessel structure to in turn locate a side branch opening. In particular, the system can be used to detect reflections or calculate energy loss due to absorption in different areas of the luminal wall. One fiber can be used as both transmitter and detector or alternatively different fiber(s) can be used either as a bundle or distributed on the circumference of the distal area of the catheter.

In another embodiment, the sensing mechanism may be located on a guidewire 70 used to deliver the system. Alternatively the sensing mechanism can be located on another elongated member exchanged with the guidewire in the central guidewire lumen 14 of the shaft 12. In all cases the sensor can be moved within the distal end of the catheter to help identify the side branch and may be moved backwards and optionally withdrawn anytime after indicating the location of the side branch.

Once the axial location of the catheter is determined using the markers 60, the sensing mechanism can be moved towards the distal end of the catheter. The operator can then rotate the catheter using feedback or other indications received from the sensing mechanism to help rotationally align the side hole in the stent with the side branch os prior to deployment of the stent.

Figure 3:
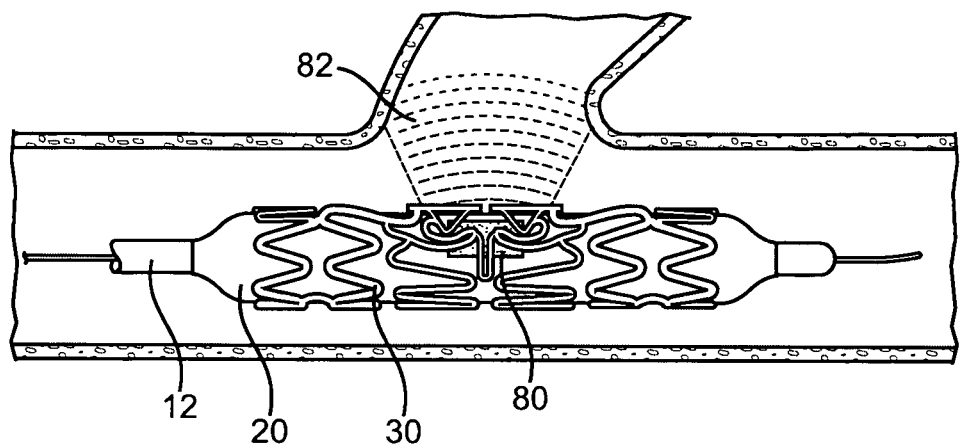
FIG. 3 shows a distal end of the catheter with a sensing mechanism to identify side branch location.

FIG. 3 illustrates a protocol which identifies the side branch using a sensing mechanism 80 located on the shaft of the catheter below the stent 30 and the balloon 20. The operator rotates the catheter shaft 12 and receives feedback from the sensing mechanism 80. As illustrated in FIG. 3, the sensing mechanism 80 comprises a sensor such as an imaging sensor having a field of view 82 passing through the side branch 40 to help indicate the location of the side branch ostium O. In other embodiments, the sensor could be an electro-chemical sensor capable of detecting proximity of the side branch. If the sensor is located near the balloon, it can detect the presence or absence of tissues. The sensing mechanism can be located at or near the distal end of the catheter 10 either within the balloon 20 or outside of the balloon.

In another embodiment, a working end of the catheter is mounted on a separate rotatable shaft with a small mechanical drive, such as a miniature electrical motor, servo mechanism, or other remotely operated drive mechanism. The operator can orient the working end of the catheter by remotely rotating the separate shaft of the catheter to achieve a correct position using any of the sensory feedback mechanisms discussed herein. Alternatively the operator can control the motion of the distal part fully or partly by using a joystick or other manual interface device that can send signal to the distal area of the catheter.

In yet another embodiment, the sensing mechanism is linked to an automatic orienting system circuit. In this embodiment the system has a controller (typically using a digital processor) to monitor the rotational position signal sent from the sensing mechanism. This signal is used to determine if the working end is accurately oriented. If it is not correctly positioned, the automatic orienting system will rotate the working end until correct orientation is achieved. In this embodiment, the system is self-aligned using a feedback loop between the sensing mechanism and the controllable electrical motor or other positioner to properly orient the stent. It is possible for the operator to deliver another wire or device to stabilize the location and orientation of the distal end. For example, the operator can deliver guidewire or fiber optics to the side branch to help stabilize the system or in some case anchor the system.

Figure 4:
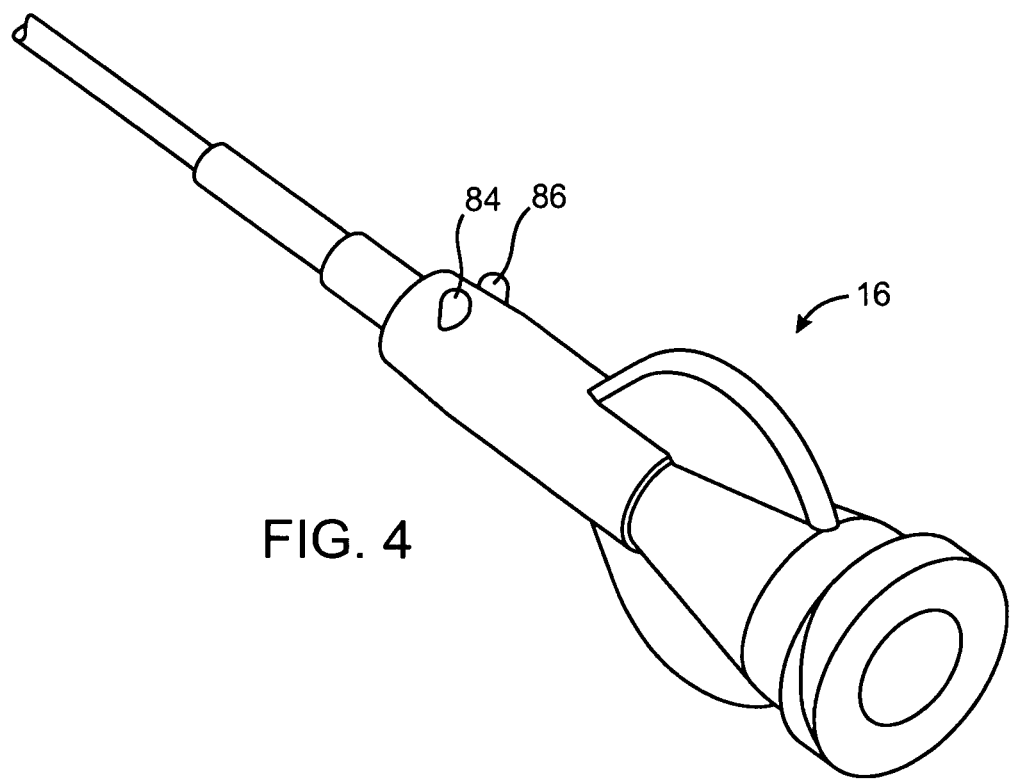
FIG. 4 shows an indicator located on a proximal hub of the catheter of FIG. 2 to provide the physician with an indication when the system is oriented properly.

FIG. 4 shows a proximal catheter hub 16 having an operator interface with a red light 84 and a green light 86 (or equivalent visual or audible signals) to notify the operator if the stent achieved the deployment position (green light) or should not deploy (red light). In this example, the power source for the sensor may be integrated with the catheter and the complete system can be a singe use system.

In one embodiment the operator interface and associated circuitry is separated from the catheter and can be used multiple times. The interface can be linked to the sensor or to a side branch locator by wireless connection or by physical connector. The power source can be integrated (battery for example) or external power source.

Figure 5:
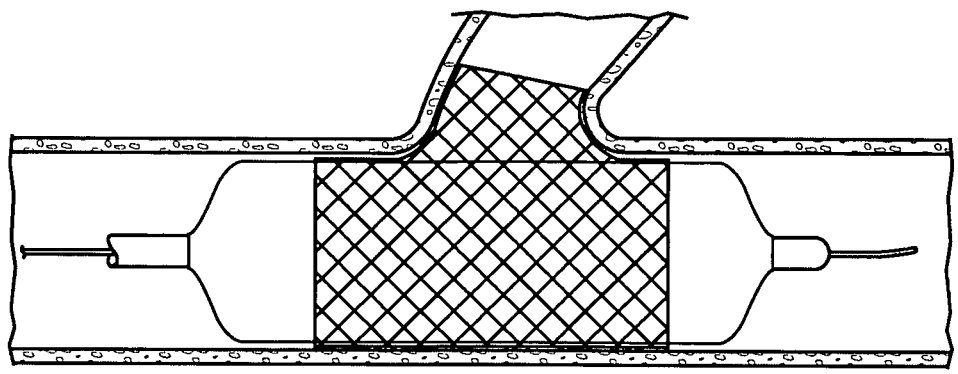
FIG. 5 shows the size of the system relative to a 3 mm reference vessel.
Figure 6:
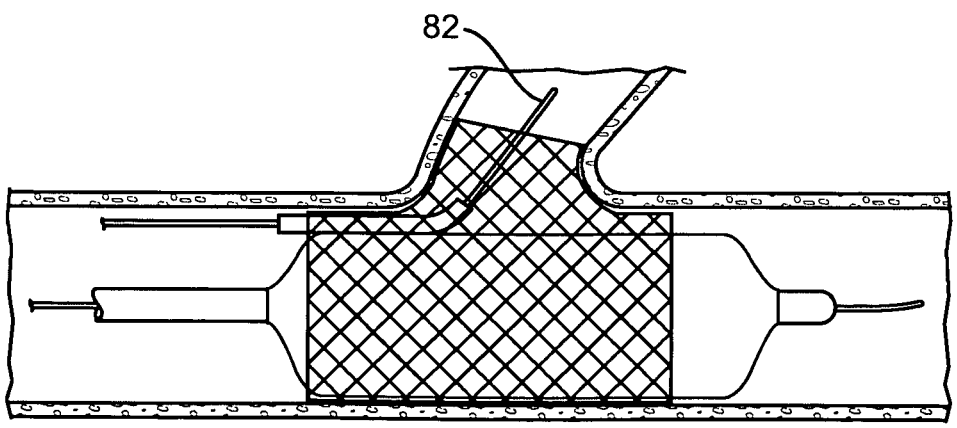
FIG. 6 shows the size of a two wire system relative to a 3 mm reference vessel.

FIG. 5 shows the profile of the system in respect to a 3 mm vessel near bifurcation area. FIG. 6 shows typical profile of a two wire system relatively to the same vessel. The benefit of the single wire system is illustrated in those figures. By eliminating the need for a second wire 86 as shown in FIG. 6 (and in come cases for a second balloon), the single wire system profile of the present invention may be 20% lower than a two wire system, usually 30% lower, and typically 50% lower. For example, the width of the stent over the balloon with the single wire (FIG. 5), will usually be no greater than 1.5 mm, preferably no greater than 1.4 mm, and often 1.2 mm or less over a portion distal to the exit point of any penetrating member through the side branch portion. In a preferred embodiment, the profile of the system is about 1 mm when designed for coronary vessels. For neuro vascular application the system may be much smaller, but for carotid application the system profile might be larger.

For coronary bifurcations, the device is usually used in vessels typically ranging from 2.5 mm to 5 mm in diameter (without stenosis). The single wire bifurcation system including the crimped coronary bifurcation stent of the present invention may be smaller than 1.5 mm and sometimes smaller than 1.4 mm, and typically close to 1.3 mm. In some cases the profile of the bifurcation stent and delivery system can be close to 1.2 mm and sometimes lower depending on the size of the stent and the specific anatomical location required. For purpose of comparison the profile of conventional non-bifurcation stents on delivery systems is usually 1.2 mm typically close to 1 mm and sometimes 0.9 mm or lower.

As a further comparison, a commonly used coronary guidewires has a diameter of approximately 0.35 mm. Typical guidewire lumen has ID (inner diameter) of 0.43 mm and OD (outer diameter) of 0.58 mm. While adding the size of the folded balloon and the wall thickness of the crimped stent (usually approximately 0.41 mm), the stack of materials alone for a dual guidewire device with dual guidewire lumens is larger than 1.4 mm. The actual profile of two wire system is typically larger than 1.5 mm usually larger than 1.6 mm and frequently as large as 1.8 mm or more. In case that a second balloon is required to inflate the side portion than the system will be in the high range of the above and sometimes even larger.

Figure 7:
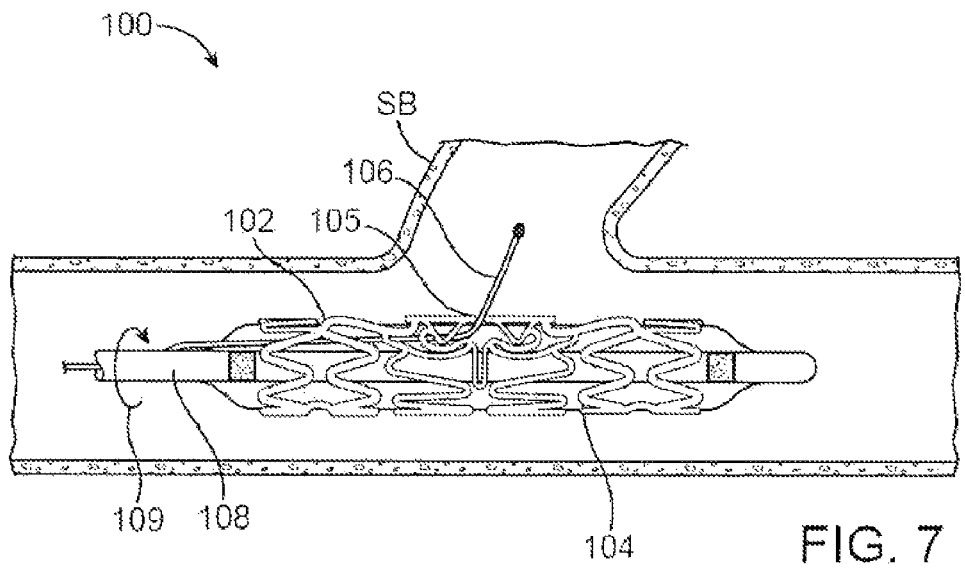
FIG. 7 shows a delivery system with "pop-up" marker to help identify side branch location.

FIG. 7 shows a single guidewire bifurcation stent delivery system 100 that utilizes a single balloon 102 to deploy a bifurcated stent 104 having a side branch portion 105. The positioning and orientation of the delivery system is obtained using a protruding, resilient ("pop-up") marker 106 that can be preloaded and released near the side branch bifurcation site SB. The marker is visible under fluoroscopic imaging. While the pop-up marker 106 is facing a vessel wall, it remains constrained. As the catheter shaft 108 is rotated (arrow 109), the pop-up marker aligns with the opening (os) of the side branch SB and enters the side branch. The appearance of the marker 106 in the side branch SB under fluoroscopic imaging indicates to the operator that the orientation is close to optimal and the stent 104 can be deployed.

In one embodiment the protruding marker has a soft tip to minimize vessel trauma. The protruding marker can be made of super elastic or shape memory alloys, such as nickel titanium, or elastic metals, such as stainless steel alloys, cobalt chromium alloys, MP35 or alike and other metals. The protruding markers can alternatively be made of a polymer such as nylon or nylon blend, pebax, or any other resilient, biocompatible polymer. Radiopaque material can be attached to the marker in order to make it visible to the operator. The radiopaque material can be crimped, swaged extruded or co-extruded, bonded or placed on the pop-up marker system in any other conventional way known to the industry. If NiTi is used while in it's shape memory state, the protruding marker can be activated by changing the temperature of the NiTi structure thereby activating a memorized shape that was applied to the marker system during processing.

Figure 8A:
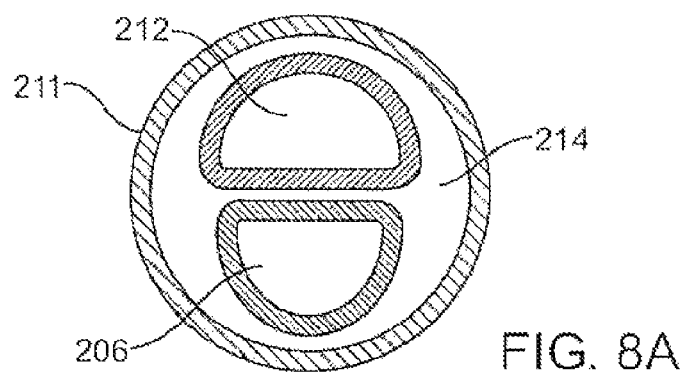
FIGS. 8A and 8B show a delivery system with a sliding marker to help identify side branch location.
Figure 8B:
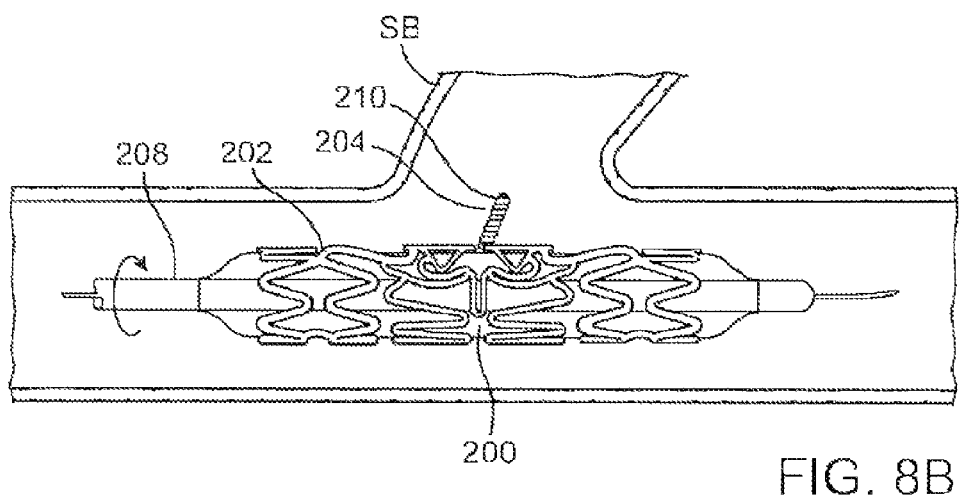

FIGS. 8A and 8B show a single wire and single balloon delivery system for bifurcation stent 200 with a side branch portion 202. In this embodiment, a moveable marker 204 can be slid in and out through a lumen 206, partial lumen, slit or one or more hooks or short lumens on the shaft 208 of the catheter. The moveable marker assembly 204 comprises an elongated member, preferably made of metallic wire or ribbon or extruded polymer such as nylon or any other material with the required physical properties that will allow pulling and/or pushing the marker assembly in its passageway. The distal end 210 of the elongated member can be made of marker material such as platinum Iridium or tungsten, or MRI visible materials, or other known marker materials currently used in the industry. Alternatively the marker material can be attached or placed or bonded or linked to the end of the marker assembly. The marker assembly can be pre shaped with a bend in such a way that when pushed out of its lumen 206 at or near the distal end of the catheter it will tend to protrude and if pushed while in proximity to a side branch SB it will appear in the side branch and can visually identified by imaging systems used in the procedure such as Ultrasound, MRI or CT. The distal end of the marker assembly 204 is designed to minimize vessel trauma when pushed against the vessel wall. Such a design may include soft tip, polymeric extension, local loop or other options. The rotatable shaft 208 consists of braided shaft section 211 with guidewire lumen 212 moveable marker lumen 206 and inflation lumen 214. The diameter of the lumen can be small and need to comply with the marker assembly dimensions. If nickel titanium or steel ribbon is used for the assembly the thickness of the material is usually 0.025 mm to 0.25 mm and sometimes in the range of 0.25 mm to 2.54 mm. The lumen can be designed to allow an interference fit for the marker, or it can be larger.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A stent delivery system comprising:
    a catheter shaft having a stent deployment region near a distal end thereof;
    a single guidewire lumen in the stent deployment region;
    a stent having a side portion on the stent deployment region of the shaft; and
    a side branch sensor on the catheter shaft, wherein the sensor comprises a resilient radiopaque penetrating element which is attached to the catheter shaft, extends under the stent and through the side portion, such that when facing a wall of a main branch vessel, the element remains constrained by the wall of the main branch vessel and when the side portion of the stent is oriented toward an ostium of a side branch vessel, the element resiliently protrudes into the side branch vessel.

2. A stent delivery system as in claim 1, wherein the stent deployment region comprises a balloon which carries the stent.

3. A stent delivery system as in claim 1, wherein the single guidewire lumen extends through the balloon which carries the stent.

4. A stent delivery system as in claim 3, wherein the width of the stent on the balloon does not exceed 1.5 mm.

5. A stent delivery system as in claim 1, wherein the resilient radiopaque penetrating element is adapted to remain constrained within the main branch vessel and to be released into the side branch vessel when aligned with the side branch vessel ostium.

6. A stent delivery system as in claim 1, wherein the resilient radiopaque penetrating element is composed of a super elastic or shape memory alloy.

7. A stent delivery system as in claim 1, wherein the resilient radiopaque penetration element is composed of a resilient polymer.

8. A method for deploying a prosthesis having a side branch portion in a side branch vessel in a main branch vessel, said method comprising:
    providing a catheter having a stent deployment region near a distal end thereof, the catheter carrying the prosthesis having the side branch portion on the stent deployment region, wherein the catheter comprises a single guidewire lumen in the stent deployment region;
    advancing the catheter in the main branch vessel over a guidewire disposed in the single guidewire lumen, the guidewire extending through the main branch vessel until the side branch portion is proximate the side branch vessel;
    rotating and/or axially positioning the catheter while observing the relative position of the side branch portion and the side branch vessel;
    deploying the prosthesis after observing the alignment of the side branch portion and the side branch vessel, wherein observing comprises probing a wall of the main branch vessel with a radiopaque probe aligned with the side branch, wherein the probe is a resilient element attached to the catheter, extending under the prosthesis and through the side branch portion such that the element remains constrained within the main branch vessel when facing the wall of the main branch vessel until the element is aligned with the side branch vessel when it resiliently pops-up and enters the side branch vessel as the catheter is rotated and/or axially positioned along the guidewire in the single guidewire lumen, the guidewire extending through the main branch vessel outside of the side branch vessel.

9. A method as in claim 8, wherein the resilient element is comprised of a super elastic or shape memory alloy.

10. A method as in claim 8, wherein the resilient element is composed of a resilient polymer.

* * * * *